United States Patent
Kokoris et al.

(10) Patent No.: US 12,116,570 B2
(45) Date of Patent: Oct. 15, 2024

(54) DIRECTED EVOLUTION OF ENZYMES BY PLASMID TAGGING IN DROPLETS

(71) Applicant: Roche Sequencing Solutions, Inc., Pleasanton, CA (US)

(72) Inventors: Mark Stamatios Kokoris, Bothell, WA (US); Michael Kovarik, Seattle, WA (US); Marc Prindle, Seattle, WA (US); Salka Keller, Shoreline, WA (US); Robert Busam, Seattle, WA (US); Miranda Lahman, Seattle, WA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 1268 days.

(21) Appl. No.: 16/337,282

(22) PCT Filed: Sep. 28, 2017

(86) PCT No.: PCT/US2017/054021
§ 371 (c)(1),
(2) Date: Mar. 27, 2019

(87) PCT Pub. No.: WO2018/064338
PCT Pub. Date: Apr. 5, 2018

(65) Prior Publication Data
US 2020/0032247 A1 Jan. 30, 2020

Related U.S. Application Data

(60) Provisional application No. 62/412,693, filed on Oct. 25, 2016, provisional application No. 62/401,780, filed on Sep. 29, 2016.

(51) Int. Cl.
| | | |
|---|---|---|
| *C12N 15/10* | (2006.01) | |
| *C12N 1/20* | (2006.01) | |
| *C12N 9/00* | (2006.01) | |
| *C12N 9/12* | (2006.01) | |
| *C12N 15/74* | (2006.01) | |
| *C40B 20/04* | (2006.01) | |
| *C40B 40/08* | (2006.01) | |

(52) U.S. Cl.
CPC ........... *C12N 15/1058* (2013.01); *C12N 1/20* (2013.01); *C12N 9/1252* (2013.01); *C12N 9/93* (2013.01); *C12N 15/74* (2013.01); *C40B 20/04* (2013.01); *C40B 40/08* (2013.01); *C12Y 207/07007* (2013.01)

(58) Field of Classification Search
None
See application file for complete search history.

(56) References Cited

U.S. PATENT DOCUMENTS

| | | |
|---|---|---|
| 7,514,210 B2 | 4/2009 | Holliger et al. |
| 7,691,576 B2 | 4/2010 | Holliger et al. |
| 8,133,673 B2 | 3/2012 | Holliger et al. |
| 8,324,360 B2 | 12/2012 | Kokoris et al. |
| 8,603,797 B2 | 12/2013 | March et al. |
| 2015/0344873 A1 | 12/2015 | Xiao et al. |
| 2020/0032247 A1* | 1/2020 | KokorisKokoris ...... C12N 9/93 |

FOREIGN PATENT DOCUMENTS

WO 2017087281 A1 5/2017

OTHER PUBLICATIONS

Brautigam, C. A. et al., Structural and functional insights provided by crystal structures of DNA polymerases and their substrate complexes, Current Opinion in Structural Biology, 1998, pp. 54-63, vol. 8.
Ghadessy, F. J. et al., Directed evolution of polymerase function by compartmentalized self-replication, PNAS, 2001, pp. 4552-4557, vol. 98, No. 8.
Ghadessy, F. J. et al., Generic expansion of the substrate spectrum of a DNA polymerase by directed evolution, Nature Biotechnology, 2004, pp. 755-759, vol. 22, No. 6.
International Preliminary Report on Patentability mailed Apr. 2, 2019 in corresponding PCT/US2017/054021 filed Sep. 28, 2017, 7 pages.
International Search Report and Written Opinion mailed Jan. 17, 2018 in corresponding PCT/US2017/054021 filed Sep. 28, 2017, 9 pages.
Loakes, D. et al., Polymerase engineering: towards the encoded synthesis of unnatural biopolymers, Chem. Commun., Royal Society of Chemistry, 2009, pp. 4619-4631.
Pinheiro et al, Synthetic genetic polymers capable of heredity and evolution, Science, 2012, 341-4. doi: 10.1126/science.1217622, 336(6079).

* cited by examiner

*Primary Examiner* — Nancy J Leith
*Assistant Examiner* — Jessica D Parisi
(74) *Attorney, Agent, or Firm* — Roche Sequencing Solutions, Inc.

(57) ABSTRACT

Methods and compositions for the selection of nucleic acid processing and other enzymes, and more specifically for the selection of DNA polymerases and other enzymes with desired properties employing the directed evolution of enzymes by plasmid tagging in droplets.

5 Claims, 10 Drawing Sheets
Specification includes a Sequence Listing.

| Comparison | Rxn temperature | Background |
|---|---|---|
| Null/WT | 50°C | 20.13 % |
| Null/Mothra | 50°C | 29.56 % |
| Null/WT | 65°C | 2.82 % |
| Null/Mothra | 65°C | 4.02 % |

FIG. 4

|  | SK/RB | MJK | MJK |
|---|---|---|---|
|  | Round 1 | Round 2 | Round 3 |
|  | CP | CP | CP |
| C342R1 | 28.8 | 29.1 | 29.8 |
| C417R1 | 25.0 | 24.9 | 24.4 |
| 105/106 A | 28.5 | 27.8 | 27.1 |
| 105/106 B | 27.0 | 27.1 | 26.3 |
| C422R1 | N/A | 26.6 | 27.8 |

| | Round 1 | Round 2 | Round 3 |
|---|---|---|---|
| 105/106 average | 27.8 | 27.5 | 26.7 |

FIG. 6

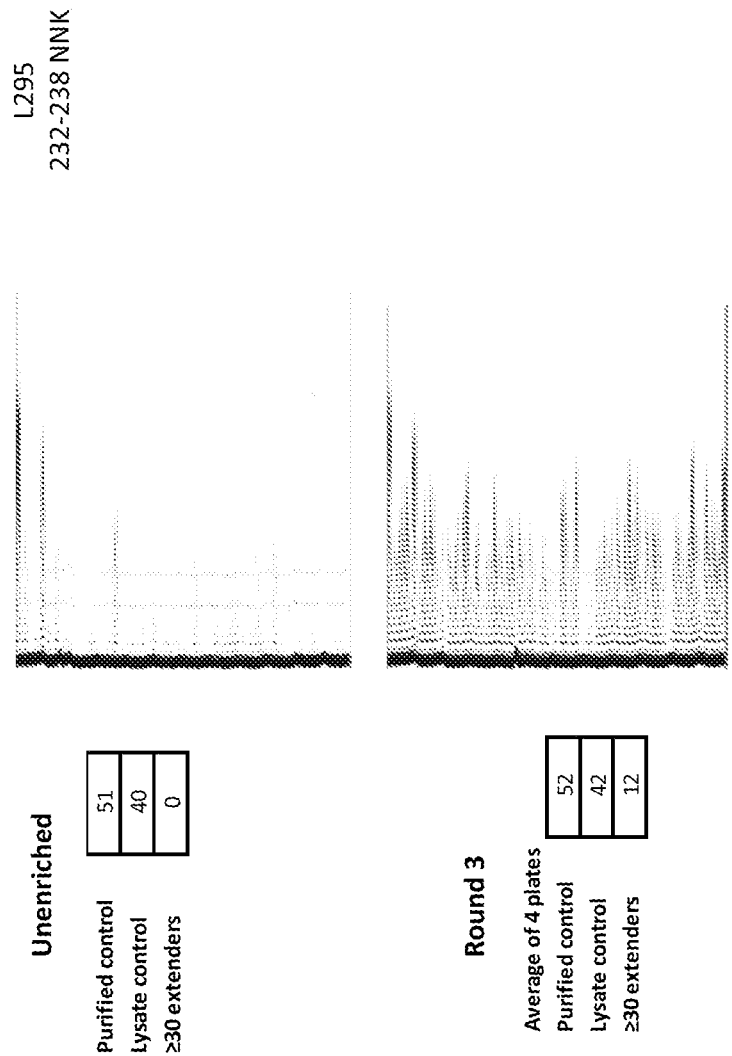

DIRECTED EVOLUTION OF ENZYMES BY PLASMID TAGGING IN DROPLETS

STATEMENT REGARDING SEQUENCE LISTING

The Sequence Listing associated with this application is provided in text format in lieu of a paper copy, and is hereby incorporated by reference into the specification. The name of the text file containing the Sequence Listing is SEQUENCE_LISTING.txt. The text file is 943B, was created on Mar. 13, 2019, and is being submitted electronically via EFS-Web.

BACKGROUND

DNA polymerases occupy a central role in the maintenance, transmission, and expression of genetic information. They have also enabled core technologies of molecular biology, such as sequencing, PCR, site-directed mutagenesis, and cDNA cloning. However, natural DNA polymerases are often not optimally suited for these applications, particularly when substrates include non-natural dNTPs. Thus, attempts have been made to tailor DNA polymerase function by using either design or selection strategies to generate variants capable of utilizing a wider range of substrates.

Structural studies have greatly advanced the understanding of DNA polymerase function (see, e.g., Joyce, C. M. and Steitz, T. A. (1998) *Curr. Opin. Struct.* Biol. 8, 54-63) and, together with insights gained from site-directed mutagenesis, have allowed rational design of some DNA polymerase variants with improved properties. Examples include variants of Taq polymerase with improved abilities to incorporate dideoxynucleotides or ribonucleotides, reduced pausing during polymerization, or altered fidelity (see, e.g., Loakes, D. and Holliger, P. (2009) *Chem. Commun.* 4619-4631)). While in vivo screening by genetic complementation has proven to be a highly effective and convenient way to identify active variants from a large library of polymerase mutants, its scope is limited by the fact that the only property that is screened for is basal polymerase activity. In vitro high-throughput screening is potentially much more flexibly as, in principle, any polymerase property can be optimized, provided it is amenable to a high-throughput assay. However, most of these assays rely on the detection of double-stranded DNA, or on the disruption of template secondary structure by the strand displacement activity of the polymerase. Such assays are not ideal for the discovery of polymerases with an enhanced ability to incorporate and replicate unnatural nucleotide substrate, as polymerase activity may be too weak for significant amounts of dsDNA to be synthesized or the chemistry of the modified substrates may interfere with dye binding or fluorescence. Other potential shortcomings include false positives, e.g., polymerases with enhanced abilities to synthesize dsDNA while avoiding the non-natural substrate and polymerases that preferentially misincorporate tagged nucleotides. In addition, in vitro screening methods are currently limited to polymerase libraries an order of magnitude smaller than those used in genetic complementation.

Larger polymerase repertoires can, in principle, be processed by the use of selection technologies. One of the most productive selection methods has been phage display, which has been adapted for the selection of polymerase activity by proximal display of both primer-template substrate and polymerase on the surface of the phage particle. One drawback to this approach, however, is that assay conditions must be compatible with phage viability, which limits the selection of polymerases that normally function under dissimilar conditions, e.g., thermophilic environments. In addition, the intramolecular tethering of the substrate and polymerase may favor the selection of polymerase variants with low affinity for template-primer duplex and/or poor processivity. Furthermore, polymerases are usually not efficiently secreted and displayed on the phage surface.

Compartmentalization methods based on water-in-oil emulsions have recently been developed for the use in polymerase repertoire selection methods. Compartmentalization segregates individual polymerase genes and their encoded proteins into discrete, physically separate aqueous compartments, thus ensuring the linkage of genotype and phenotype during the selection process. Holliger and colleagues (see, e.g., U.S. Pat. No. 7,514,210 to Holliger et al.) have described one approach, termed compartmentalized self-replication (CSR) that is based on a simple feedback loop, in which a polymerase replicates only its own encoding gene with compartmentalization into the aqueous compartments of a water-in-oil emulsion serving to isolate individual self-replication reactions from each other. Thus each polymerase replicates only its own encoding gene to the exclusion of those in other compartments (i.e. self-replicates). In such a system adaptive gains directly translate into genetic amplification of the encoding gene. Therefore, the copy number of a polymerase gene after one round of CSR is correlated to the catalytic activity of the encoded polymerase under the selection conditions, with polymerase genes encoding the most active mutants best adapted to the selection conditions dominating the population. CSR has proved to be a productive method for the selection of polymerase function yielding variants of Taq polymerase with >10-fold increased thermostability >130-fold increased resistance to heparin (see, e.g., Ghadessy, F. J. et al. (2001) *Proc. Natl. Acad. Sci.* 98, 4552-4557), or a genetically enhanced substrate spectrum (see, e.g., Ghadessy, F. J. et al. (2004) Nat. Biotechnol. 22, 755-759). However, CSR makes stringent demands on the catalytic efficiency and processivity of selected polymerases.

In order to reduce the adaptive burden and increase the sensitivity of the CSR method, Holliger and colleagues developed an alternative approach, termed compartmentalized self-tagging (CST), to generate polymerases with lower catalytic turnover, e.g., those with the ability to incorporate modified nucleotides or other non-natural substrates in cases where those modifications preclude replication of the extension product (see, e.g., U.S. Pat. No. 7,691,576 to Holliger and Oliynyk). CST is based on a positive feedback loop whereby a polymerase tags the plasmid containing its gene by extending a biotinylated primer. Primer extension stabilizes the metastable primer-plasmid complex allowing capture in proportion to its stability. After selection, genes encoding the desired enzymatic activities are isolated through bead capture and recovered plasmid DNA is amplified and used to start a new round of selection or screening. Using CST selections performed on libraries of a variant of the replicative polymerase of *Thermococcus gorgonarius*, Holliger and colleagues reported evolution of polymerases capable of processive synthesis of synthetic genetic polymers ("XNAs") based on substrates in which the canonical ribofuranose ring of DNA or RNA was replaced by five or six-membered congeners comprising HNA, CeNA, LNA, ANA, FANA, and TNA from a DNA template (see, e.g., Pinheiro, V. B. et al. (2012) *Science* 336(6079), 341-344). Despite such achievements, successful application of the CST method requires overcoming the technical challenges associated with generation and capture of a metastable primer-plasmid complex, e.g., melting of the parent plasmid to create a strand invasion bubble, or strand displacement by a heterologous, low affinity primer and subsequent stable annealing of the primer to provide a free 3' end for template-dependent DNA replication.

Recently, Kokoris et al. have described a method, termed "sequencing by expansion" (SBX), that uses a DNA polymerase to transcribe the sequence of DNA onto a measurable polymer referred to as an "Xpandomer" (see, e.g., U.S. Pat. No. 8,324,360 to Kokoris et al.). The transcribed sequence is encoded along the Xpandomer backbone in high signal-to-noise reporters that are separated by ~10 nm and are designed for high signal-to-noise, well differentiated responses when read by nanopore-based sequencing systems. Xpandomers are generated from non-natural nucleotide analogs, referred to as XNTPs, which are characterized by bulky substituents that enable the Xpandomer backbone to be expanded following synthesis. However, XNTPs introduce significant challenges to natural DNA polymerases due to the extraordinary substrate specificities of these enzymes.

Thus, despite advances in enzyme engineering, there remains a need for improved methods capable of producing novel "designer" enzymes, such as DNA polymerases with expanded substrate ranges for SBX and other biotechnology applications. The present invention fulfills these needs and provides other related advantages.

BRIEF SUMMARY

In brief, methods and compositions are provided for the selection of an enzyme capable of modifying a nucleic acid that is not dependent on the complete replication of the enzyme-encoding gene.

In one embodiment, the method includes the steps of (a) providing a parent nucleic acid encoding an enzyme of interest, in which the parent nucleic acid provides the gene sequence of the enzyme of interest and wherein the parent nucleic acid is provided in a host cell; (b) providing conditions to induce the host cell to produce the enzyme of interest; (c) following production of the enzyme of interest by the host cell, compartmentalizing the host cell according to step (a), such that the compartment includes the parent nucleic acid together with the enzyme of interest encoded by the parent nucleic acid; (d) providing conditions to cleave at least one strand of the parent nucleic acid to provide at least one free 3' end and at least one free 5' end; (e) providing conditions such that at least one of the free 3' ends or at least one of the free 5' ends of the parent nucleic acid is modified by the enzyme of interest to yield a modified parent nucleic acid comprising a molecular tag; and (f) isolating the modified parent nucleic acid.

In certain embodiments, the enzyme of interest may be a DNA polymerase or a DNA ligase. In one embodiment, the enzyme is a class Y DNA polymerase. In a further embodiment, the enzyme is a DPO4 polymerase.

In another embodiment, the conditions to cleave at least one strand of the parent nucleic acid include exposing the parent nucleic acid to a restriction endonuclease. In a further embodiment, the restriction endonuclease is a nickase. In yet another embodiment, the nickase is Nt.BspQ1. In other embodiments, the conditions to cleave at least one strand of the parent nucleic acid linearize the parent nucleic acid. In another embodiment, the modified nucleic acid comprises XNTPs.

In another embodiment, a convertible parental expression plasmid is provided for conducting directed evolution of enzymes by plasmid tagging in droplets (DEEPid) including at least one recognition sequence for at least one nickase enzyme. In some embodiments, the convertible parental expression plasmid includes two recognition sequences for at least one nickase enzyme. In other embodiments, the two recognition sequences are on opposite strands of the plasmid. In yet other embodiments, the two recognition sequences are separated by from around 4 to around 20 nucleotides. In a further embodiment, the two recognition sequences are separated by at least one challenge sequence.

BRIEF DESCRIPTION OF THE SEVERAL VIEWS OF THE DRAWINGS

FIG. 4 shows results of an initial three polymerase DEEPid selection experiment.

FIG. 6 shows results from DEEPid applied to a small library of DPO4 polymerase variants.

FIGS. 7A-7D are gels showing results from three rounds of DEEPid selection applied to four different libraries of DPO4 polymerase variants.

DETAILED DESCRIPTION OF THE INVENTION

Definitions

Figure 1:
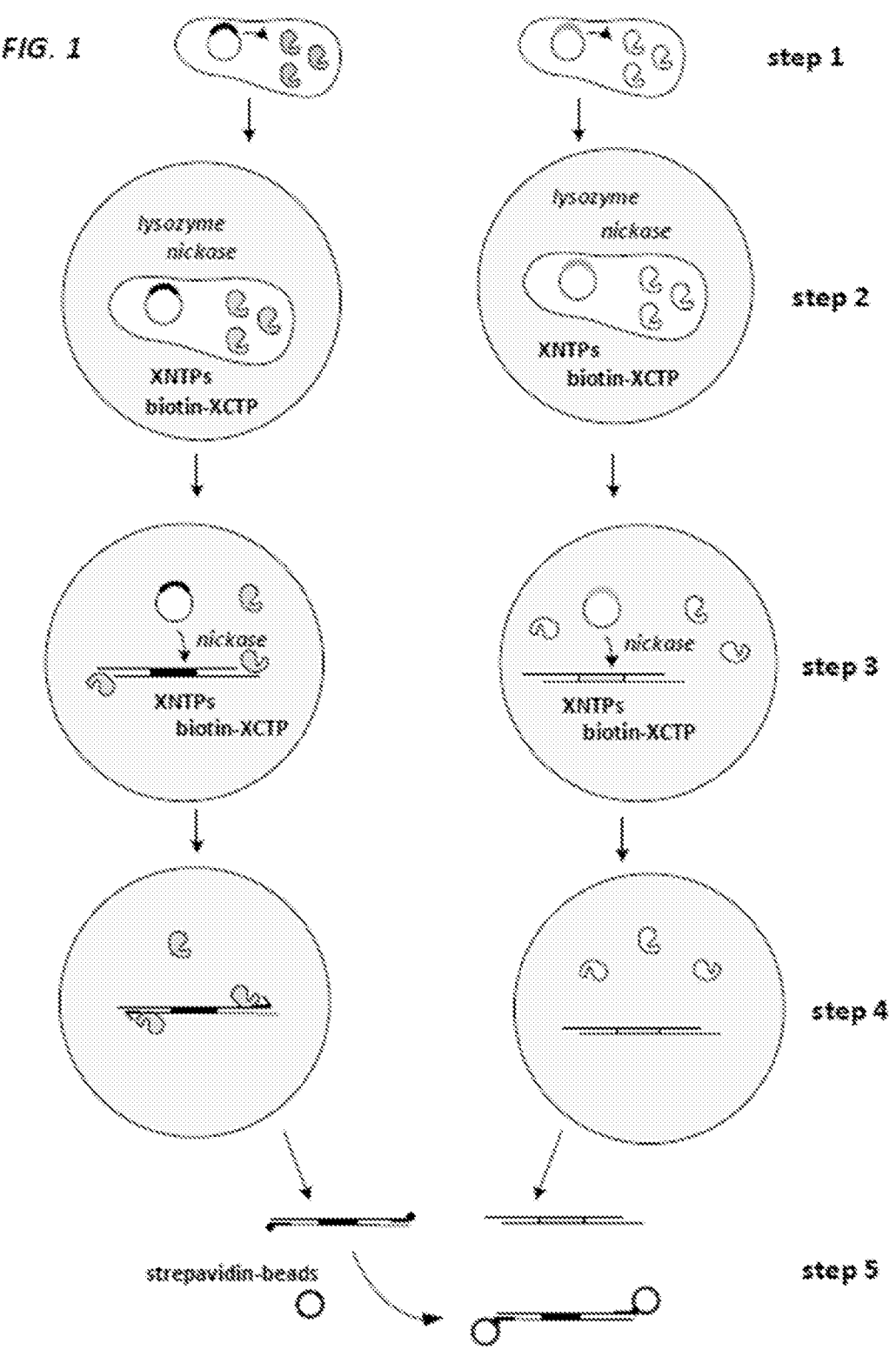
FIG. 1 illustrates one embodiment of the directed evolution of enzymes by plasmid tagging in droplets (DEEPid) methodology.

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like.

The term "about" as used herein indicates the value of a given quantity varies by +/−10% of the value, or optionally +/−5% of the value, or in some embodiments, by +/−1% of the value so described.

"Nucleobase" is a heterocyclic base such as adenine, guanine, cytosine, thymine, uracil, inosine, xanthine, hypoxanthine, or a heterocyclic derivative, analog, or tautomer thereof. A nucleobase can be naturally occurring or synthetic. Non-limiting examples of nucleobases are adenine, guanine, thymine, cytosine, uracil, xanthine, hypoxanthine, 8-azapurine, purines substituted at the 8 position with methyl or bromine, 9-oxo-N6-methyladenine, 2-aminoadenine, 7-deazaxanthine, 7-deazaguanine, 7-deaza-adenine, N4-ethanocytosine, 2,6-diaminopurine, N6-ethano-2,6-diaminopurine, 5-methylcytosine, 5-(C3-C6)-alkynylcytosine, 5-fluorouracil, 5-bromouracil, thiouracil, pseudoisocytosine, 2-hydroxy-5-methyl-4-triazolopyridine, isocytosine, isoguanine, inosine, 7,8-dimethylalloxazine, 6-dihydrothymine, 5,6-dihydrouracil, 4-methyl-indole, ethenoadenine and the non-naturally occurring nucleobases described in U.S. Pat. Nos. 5,432,272 and 6,150,510 and PCT applications WO 92/002258, WO 93/10820, WO 94/22892, and WO 94/24144, and Fasman ("Practical Handbook of Biochemistry and Molecular Biology", pp. 385-394, 1989, CRC Press, Boca Raton, La.), all herein incorporated by reference in their entireties.

"Nucleobase residue" includes nucleotides, nucleosides, fragments thereof, and related molecules having the property of binding to a complementary nucleotide. Deoxynucleotides and ribonucleotides, and their various analogs, are contemplated within the scope of this definition. Nucleobase residues may be members of oligomers and probes. "Nucleobase" and "nucleobase residue" may be used interchangeably herein and are generally synonymous unless context dictates otherwise.

"Polynucleotides", also called nucleic acids, are covalently linked series of nucleotides in which the 3' position of the pentose of one nucleotide is joined by a phosphodiester group to the 5' position of the next. DNA (deoxyribonucleic acid) and RNA (ribonucleic acid) are biologically occurring polynucleotides in which the nucleotide residues are linked in a specific sequence by phosphodiester linkages. As used herein, the terms "polynucleotide" or "oligonucleotide" encompass any polymer compound having a linear backbone of nucleotides. Oligonucleotides, also termed oligomers, are generally shorter chained polynucleotides.

"Nucleic acid" is a polynucleotide or an oligonucleotide. A nucleic acid molecule can be deoxyribonucleic acid (DNA), ribonucleic acid (RNA), or a combination of both. Nucleic acids are generally referred to as "target nucleic acids" or "target sequence" if targeted for sequencing. Nucleic acids can be mixtures or pools of molecules targeted for sequencing.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

A "polypeptide" is a polymer comprising two or more amino acid residues (e.g., a peptide or a protein). The polymer can additionally comprise non-amino acid elements such as labels, quenchers, blocking groups, or the like and can optionally comprise modifications such as glycosylation or the like. The amino acid residues of the polypeptide can be natural or non-natural and can be unsubstituted, unmodified, substituted or modified.

An "amino acid sequence" is a polymer of amino acid residues (a protein, polypeptide, etc.) or a character string representing an amino acid polymer, depending on context.

Numbering of a given amino acid or nucleotide polymer "corresponds to numbering of" or is "relative to" a selected amino acid polymer or nucleic acid when the position of any given polymer component (amino acid residue, incorporated nucleotide, etc.) is designated by reference to the same residue position in the selected amino acid or nucleotide polymer, rather than by the actual position of the component in the given polymer. Similarly, identification of a given position within a given amino acid or nucleotide polymer is "relative to" a selected amino acid or nucleotide polymer when the position of any given polymer component (amino acid residue, incorporated nucleotide, etc.) is designated by reference to the residue name and position in the selected amino acid or nucleotide polymer, rather than by the actual name and position of the component in the given polymer. Correspondence of positions is typically determined by aligning the relevant amino acid or polynucleotide sequences.

The term "recombinant" indicates that the material (e.g., a nucleic acid or a protein) has been artificially or synthetically (non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is, e.g., a polypeptide or protein which is produced by expression of a recombinant nucleic acid.

"Template-directed synthesis", "template-directed assembly", "template-directed hybridization", "template-directed binding" and any other template-directed processes, e.g., primer extension, refers to a process whereby nucleotide residues or nucleotide analogs bind selectively to a complementary target nucleic acid, and are incorporated into a nascent daughter strand. A daughter strand produced by a template-directed synthesis is complementary to the single-stranded target from which it is synthesized. It should be noted that the corresponding sequence of a target strand can be inferred from the sequence of its daughter strand, if that is known. "Template-directed polymerization" is a special case of template-directed synthesis whereby the resulting daughter strand is polymerized.

"XNTP" is an expandable, 5' triphosphate modified nucleotide substrate compatible with template dependent enzymatic polymerization. An XNTP has two distinct functional components; namely, a nucleobase 5'-triphosphate and a tether or tether precursor that is attached within each nucleotide at positions that allow for controlled RT expansion by intra-nucleotide cleavage.

"Xpandomer intermediate" is an intermediate product (also referred to herein as a "daughter strand") assembled from XNTPs, and is formed by a template-directed assembly of XNTPs using a target nucleic acid template. The Xpandomer intermediate contains two structures; namely, the constrained Xpandomer and the primary backbone. The constrained Xpandomer comprises all of the tethers in the daughter strand but may comprise all, a portion or none of the nucleobase 5'-triphosphates as required by the method. The primary backbone comprises all of the abutted nucleobase 5'-triphosphates. Under the process step in which the primary backbone is fragmented or dissociated, the constrained Xpandomer is no longer constrained and is the Xpandomer product which is extended as the tethers are stretched out. "Duplex daughter strand" refers to an Xpandomer intermediate that is hybridized or duplexed to the target template.

"Xpandomer" or "Xpandomer product" is a synthetic molecular construct produced by expansion of a constrained Xpandomer, which is itself synthesized by template-directed assembly of XNTPs. The Xpandomer is elongated relative to the target template it was produced from. It is composed of a concatenation of XNTPs, each XNTP including a tether comprising one or more reporters encoding sequence information. The Xpandomer is designed to expand to be longer than the target template thereby lowering the linear density of the sequence information of the target template along its length. In addition, the Xpandomer optionally provides a platform for increasing the size and abundance of reporters which in turn improves signal to noise for detection. Lower linear information density and stronger signals increase the resolution and reduce sensitivity requirements to detect and decode the sequence of the template strand.

"Tether" or "tether member" refers to a polymer or molecular construct having a generally linear dimension and with an end moiety at each of two opposing ends. A tether is attached to a nucleobase 5'-triphosphate with a linkage in at least one end moiety to form an XNTP. The end moieties of the tether may be connected to cleavable linkages to the nucleobase 5'-triphosphate that serve to constrain the tether in a "constrained configuration". After the daughter strand is synthesized, each end moiety has an end linkage that couples directly or indirectly to other tethers. The coupled tethers comprise the constrained Xpandomer that further comprises the daughter strand. Tethers have a "constrained configuration" and an "expanded configuration". The constrained configuration is found in XNTPs and in the daughter strand. The constrained configuration of the tether is the precursor to the expanded configuration, as found in Xpandomer products. The transition from the constrained configuration to the expanded configuration results in cleaving of selectively cleavable bonds that may be within the primary backbone of the daughter strand or intra-tether linkages. A tether in a constrained configuration is also used where a tether is added to form the daughter strand after assembly of the "primary backbone". Tethers can optionally comprise one or more reporters or reporter constructs along its length that can encode sequence information of substrates. The tether provides a means to expand the length of the Xpandomer and thereby lower the sequence information linear density.

"Tether element" or "tether segment" is a polymer having a generally linear dimension with two terminal ends, where the ends form end-linkages for concatenating the tether elements. Tether elements may be segments of tether constructs. Such polymers can include, but are not limited to: polyethylene glycols, polyglycols, polypyridines, polyisocyanides, polyisocyanates, poly(triarylmethyl)methacrylates, polyaldehydes, polypyrrolinones, polyureas, polyglycol phosphodiesters, polyacrylates, polymethacrylates, polyacrylamides, polyvinyl esters, polystyrenes, polyamides, polyurethanes, polycarbonates, polybutyrates, polybutadienes, polybutyrolactones, polypyrrolidinones, polyvinylphosphonates, polyacetamides, polysaccharides, polyhyaluranates, polyamides, polyimides, polyesters, polyethylenes, polypropylenes, polystyrenes, polycarbonates, polyterephthalates, polysilanes, polyurethanes, polyethers, polyamino acids, polyglycines, polyprolines, N-substituted polylysine, polypeptides, side-chain N-substituted peptides, poly-N-substituted glycine, peptoids, side-chain carboxyl-substituted peptides, homopeptides, oligonucleotides, ribonucleic acid oligonucleotides, deoxynucleic acid oligonucleotides, oligonucleotides modified to prevent Watson-Crick base pairing, oligonucleotide analogs, polycytidylic acid, polyadenylic acid, polyuridylic acid, polythymidine, polyphosphate, polynucleotides, polyribonucleotides, polyethylene glycol-phosphodiesters, peptide polynucleotide analogues, threosyl-polynucleotide analogues, glycol-polynucleotide analogues, morpholino-polynucleotide analogues, locked nucleotide oligomer analogues, polypeptide analogues, branched polymers, comb polymers, star polymers, dendritic polymers, random, gradient and block copolymers, anionic polymers, cationic polymers, polymers forming stem-loops, rigid segments and flexible segments.

General Strategy of the Method of the Invention

A method for the selection of an enzyme capable of modifying a nucleic acid wherein the method is not dependent on the complete replication of the enzyme-encoding gene, which method comprises the steps of:
(a) providing a parent nucleic acid encoding an enzyme of interest, wherein the parent nucleic acid provides the gene sequence of the selected enzyme of interest, and wherein the parent nucleic acid is provided in a host cell;
(b) providing conditions to induce the host cell to produce the enzyme of interest;
(c) following production of the enzyme of interest by the host cell, compartmentalizing the host cell according to step (a), such that the compartment comprises the parent nucleic acid together with the enzyme of interest encoded by the parent nucleic acid;
(d) providing conditions to cleave at least one strand of the parent nucleic acid to provide at least one free 3' end and at least one free 5' end;
(e) providing conditions such that the at least one free 3' end or the at least one free 5' end of the parent nucleic acid is modified by the enzymes of interest to yield a modified parent nucleic acid comprising a molecular tag; and
(f) isolating the modified parent nucleic acid. \

In some embodiments, a plurality of parent nucleic acids encoding a plurality of enzymes of interest are employed in the method disclosed above, and the step of compartmentalization involves the generation of a plurality of compartments, each of which includes a parent nucleic acid together with an enzyme of interest encoded by the parent nucleic acid.

In one embodiment, the disclosed methods include the following general steps:
expression of an enzyme of interest from parental nucleic acids, preferably from plasmids in whole cells prior to compartmentalization;
cleaving the parental nucleic acid, preferably by digesting the plasmid with a restriction endonuclease to produce at least one free 3' end and at least one free 5' end;
modification of the cleaved parental nucleic acid by the enzyme of interest, preferably by template-dependent extension of the free 3' end with non-natural nucleotide substrates, at least one of which includes a molecular tag; and
isolation of the modified parental nucleic acid via the tag.

In certain embodiments, the methods may be referred to as "directed evolution of enzymes by plasmid tagging in droplets" (DEEPid), and has the features noted below.

By providing the free 3' end(s) for modification by the enzyme of interest within the parent nucleic acid itself, many of the problems of existing methods which require formation of an artificial primosome, (e.g., providing conditions to open up a region of duplex DNA followed by strand invasion of a heterologous oligonucleotide such that it can anneal to one of the two strands of the melted duplex DNA "bubble", to provide a free 3' end for extension) are overcome. Moreover, optimizing conditions to efficiently isolate a metastable modified oligonucleotide/plasmid hybrid are not necessary according to the methods of the present invention.

Furthermore, the use of plasmids to express the enzyme of interest means that such expression may occur within whole cells, which comprise all the machinery required for the expression and processing of the enzyme of interest. Likewise, expressing the enzyme of interest from plasmids overcomes many of the problems posed by attempting such selection methods using linear DNA.

'Free 3' Ends' and 'Free 5' Ends'

The term 'a free 3' end' refers to an extendable hydroxyl moiety on the third carbon of the terminal sugar ring of a stretch of double-stranded nucleic acid, e.g., a 3' OH substrate for extension of a nucleic acid. In certain embodiments, the free 3' end primes synthesis of a modified nucleic acid strand by a strand-displacing DNA polymerase. Conversely, the term 'a free 5' end' refers to the end of a nucleic acid strand that has the fifth carbon in the sugar ring at its terminus with an attached phosphate group that is accessible for a chemical reaction, e.g., a ligation reaction to a free 3' end.

Providing free 3' ends and free 5' ends is application-dependent, and depends upon, e.g., the sequence of the parent nucleic acid and the selection conditions. In some embodiments, free 3' ends and free 5' ends are provided by nicking (hydrolysis) of at least one strand of the phosphodiester backbone of dsDNA by a restriction endonuclease. The restriction endonuclease (RE) may be any suitable enzyme known in the art, e.g., Type II RE (Type IIS, IIB, IIG, etc.), Type I RE, or a Type III RE.

In one embodiment, the free 3' ends and free 5' ends are produced by digesting the parent nucleic acid with a nickase enzyme. Nickases include endonucleases that recognize a specific recognition sequence in a double-stranded nucleic acid, and cut one strand at a specific location relative to the recognition sequence, thereby giving rise to single-stranded breaks in the double-stranded nucleic acid. Examples of nickases include Nb.BbvCI, Nb.BsmI, Nb.BsrDI, Nb.BtsI, Nt.AlwI, Nt.BbvCI, Nt.BsmAI, Nt.BspQI, NtBstNBI, and Nt.CviPII. Conditions using nickases to generate single-stranded breaks in double-stranded nucleic acids, such as plasmid DNA, are well known in the art. In certain embodiments the methods of the present invention include the step of using a nickase enzyme to produce a linearized parental plasmid with two free 3' ends and two 5' single stranded "overhangs".

In other embodiments, free 3' and free 5' ends can be produced in a double-stranded nucleic acid by other biochemical (e.g., limited digestion with a non-specific endonuclease or exonuclease), chemical (e.g., exposure to elevated pH or treatment with a base), or physical (e.g. physical shearing) means.

'Modification of a Free 3' End'

The term 'modification of a free 3' end' refers to an alteration in the structure of the free 3' end. Such alterations include but are not limited to any one or more of the group consisting of the following: polymeric extension of the 3' end with natural or non-natural (e.g. substituted) nucleotide substrates; ligation of a nucleotide or an oligonucleotide to the 3' end; phosphorylation of the 3' end followed by tag ligation as herein described; conversion of an entity linked to the 3' end to a different entity, for example attachment of a molecular group to the extending 3' end, for example $H_2O_2$, HRP or biotin tyramide.

Modification of the free 3' end may be direct or indirect. However, in either case, the result of free 3' end modification is that a molecular tag is incorporated into the parent nucleic acid. This molecular tag allows the subsequent isolation of the parent nucleic acid.

'Modification of a Free 5' End'

The term 'modification of a free 5' end' refers to an alteration in the structure of the free 5' end. Such alterations include but are not limited to any one or more of the group consisting of the following: ligation of a nucleotide or an oligonucleotide to the 5' end; phosphorylation of the 5' end followed by tag ligation as herein described; conversion of an entity linked to the 5' end to a different entity, for example attachment of a molecular group to the extending 5' end, for example $H_2O_2$, HRP or biotin tyramide.

Modification of the free 5' end may be direct or indirect. However, in either case, the result of free 5' end modification is that a molecular tag is incorporated into the parent nucleic acid. This molecular tag allows the subsequent isolation of the parent nucleic acid.

Molecular Tags/Isolation Tags.

The details of the method of incorporation of molecular tags into modified free 3' ends or modified 5' ends according to the invention will depend upon the properties of the enzyme of interest.

For example, in the case that the enzyme of interest is a DNA polymerase then incorporation of one or more tagged nucleotides into the 3' end of the DNA sequence is used to incorporate a molecular tag into the genetic element using the DNA polymerase. Furthermore, in the case that the enzyme of interest is a ligase, then the molecular tag is incorporated into the modified nucleic acid via the ligation of a tagged oligonucleotide to the free 3' end or free 5' end which is associated with the nucleic acid according to the invention. Furthermore, in the case that the enzyme of interest is a polynucleotide kinase, then incorporation of a molecular tag occurs via the 5' phosphorylation and ligation of an oligonucleotide which bears a molecular tag.

In the case where the molecular tag is a tagged nucleotide, the nucleotide triphosphate mix within a compartment according to the invention is spiked with a (or several) nucleotides modified with a molecular tag, e.g. biotin-dNTP. After extension and incorporation, the modified parental nucleic acid becomes decorated with tag molecules (e.g. biotin), allowing its isolation.

Tagged nucleotides themselves may be non-natural substrates (such as an XNTP as described herein) and thus their incorporation may select directly for the sought after phenotype. Alternatively, incorporation may be an indication of polymerase activity under the selection conditions or an ability to extend a modified 3' end.

Suitable molecular tags include biotin, digoxigenin (DIG), fluorescein (FITC), di-nitrophenol (DNP) etc., which can be captured using avidin/streptavidin or suitable antibodies. Alternatively, the nucleotide may be modified to display a free amino group (NH2), which can be specifically modified post extension with a suitable tag.

Multiple tags may offer the possibility of two (or multi-) step isolation and selection schemes, or isolation schemes with combinations of selection requirements, e.g. isolate all molecules with A or B, or all molecules with A and B, or molecules with A but not B.

Enzymes for Selection According to the Methods of the Invention.

The methods disclosed herein are particularly suitable for the selection of enzymes, particularly nucleic acid modifying enzymes, which have any one or more of the following characteristics: low catalytic turnover, low substrate processivity, nucleic acid modifying enzymes which incorporate modified nucleotide substrates and polymerases with an ability to incorporate highly substituted nucleotide analogs, e.g., XNTPs.

Suitable enzymes for selection using the disclosed methods include any one or more of those selected from the group consisting of the following: nucleic acid modifying enzymes, enzymes which act on one or more substrates of nucleic acid replicases (that is, enzymes indirectly involved in nucleic acid processing), enzymes which modulate the activity of replicases (that is, enzymes indirectly involved in nucleic acid processing), enzymes which act directly on a substrate molecule linked to a free 3' end within a region of a plasmid encoding that enzyme according to the method of the invention, enzymes which act indirectly on a substrate molecule linked to a free 3' end.

Suitable nucleic acid modifying enzymes include any of those selected from the group consisting of the following: replicases, in particular DNA polymerases; DNA ligases, RNA ligases, and polynucleotide kinases.

In particular embodiments, DEEPid is useful for the selection of polymerases, which are naturally poorly processive, such as members of the PolY or PolX family or low-processivity variants of high processivity polymerases such as the Stoffel fragment of Taq polymerase or T7 DNA polymerase in the absence of thioredoxin. Alternatively, starting from a highly active and processive polymerase, DEEPid may allow evolution of variants with greatly altered turn-over and/or processivity, such as are likely to be encountered when making changes to substrate or extension chemistry.

In further embodiments, DEEPid is useful for the selection of variants of a DPO4-type DNA polymerase, which is a DNA polymerase naturally expressed by the archaea, *Sulfolobus solfataricus*, or a related Y-family DNA polymerase, which generally function in the replication of damaged DNA by a process known as translesion synthesis (TLS). Y-family DNA polymerases are homologous to the DPO4 polymerase; examples include the prokaryotic enzymes, PolII, PolIV, PolV, the archaeal enzyme, Dbh, and the eukaryotic enzymes, Rev3p, Rev1p, Pol η, REV3, REV1, Pol Ι, and Pol κ DNA polymerases, as well as chimeras thereof.

Convertible Parental Plasmid Constructs

A convertible parental plasmid construct is a parental expression plasmid engineered to contain one or more recognition sites for cleavage by a nickase enzyme. The number of cleavage sites will determine the number of free 3' ends and free 5' ends available for modification by the enzyme of interest that is expressed from the parental plasmid. In one embodiment, the parental plasmid is modified to contain two closely spaced cleavage sites on opposite strands of the plasmid. Cleavage at these sites by a nickase enzyme results in linearization of the parental plasmid, leaving two 5' overhangs (OHs). The length of the 5' OHs generated is thus determined by the spacing between the two nickase cleavage sites. In some embodiments, the cleavage sites are spaced from around 4 to around 20 nucleotides. Advantageously, these 5' OHs can serve as templates for DNA polymerases extending from the two free 3' ends of the linearized plasmid. Standard molecular biology technologies can be used to engineer cleavage sites into parental plasmids. When designing convertible modified parental plasmid constructs, it is important to confirm that the nickase-specific recognition sequence is not present in the unmodified parental plasmid.

In some embodiments, the parental DEEPid plasmid may be engineered to produce a template that introduces certain "challenges" or "stresses" to the enzyme of interest that allow for enrichment for a specific activity. For example, in one embodiment, the enzyme of interest is a DNA polymerase and the specific activity selected for is the ability to extend a free 3' by at least ten nucleotides followed by incorporation of a dGTP analog. In this embodiment, the DEEPid plasmid is engineered to contain two nickase sites on opposite strands of the plasmid separated by a sequence of at least 11 base pairs in which the first 10 base pairs lack a G/C base pair and in which the eleventh base pair is a G/C base pair.

Parental plasmids are familiar to those skilled in the art. Advantageously, the plasmids are small, on the order of less than 10 kB and have a high copy number. Such plasmids include but are not limited to any one or more of the following: colE1 or p15 origin of replication such as derivatives of pUC, pBR322, pACYC184 or pACYC177.

Compartments/Microcapsules/Droplets

The compartments (i.e. microcapsules or droplets) posses several physical properties. First, to ensure that the plasmids and protein products do not diffuse between compartments, the contents of each compartment must be isolated from the contents of the surrounding compartments, so that there is no or little exchange of the plasmid and protein products between the compartments during the experiment. Second, there should only be one type of plasmid per compartment. There can be multiple copies but they should be identical, i.e. each compartment contains a clone (one or many copies of one plasmid A but not a mixture of plasmids A, B, C etc.) of plasmids per compartment. This ensures that the protein product of an individual plasmid will be isolated from other plasmids. Thus, coupling between plasmids and protein product will be highly specific. The enrichment factor is greatest with on average one or fewer plasmids per compartment, the linkage between nucleic acid and the activity of the encoded protein being as tight as is possible, since the protein product of an individual plasmid will be isolated from the products of all other plasmids. Third, the formation and the composition of the compartments should not impair the expression of the plasmids and the activity of the protein products.

Consequently, suitable microencapsulation systems fulfil these three requirements. The appropriate system(s) may vary depending on the precise nature of the requirements in each application of the invention.

A wide variety of microencapsulation/compartmentalization procedures to produce droplets are available and may be used to create the compartments used in accordance with the present invention (see e.g., Ghadessy, F. J. et al. (2001) PNAS 98(8), 4552-4557; Levy, M. and Ellington, A. D. (2008) Chemistry and Biology 15, 979-989; and Lu, W. C. et al. (2014) *Biotechnology and Bioengineering* 111(6), 1071-1081).

These include membrane enveloped aqueous vesicles such as lipid vesicles (liposomes) and non-ionic surfactant vesicles. These are closed-membranous capsules of single or multiple bilayers of non-covalently assembled molecules, with each bilayer separated from its neighbor by an aqueous compartment. In the case of liposomes the membrane is composed of lipid molecules; these are usually phospholipids but sterols such as cholesterol may also be incorporated into the membranes. A variety of enzyme-catalyzed biochemical reactions, including RNA and DNA polymerization, can be performed within liposomes.

In one embodiment, the droplets are formed from bulk emulsions; heterogeneous systems of two immiscible liquid phases with one of the phases dispersed in the other as droplets of microscopic or colloidal size.

Emulsions may be produced from any suitable combination of immiscible liquids. Preferably the emulsion of the present invention has water (containing the biochemical components) as the phase present in the form of finely divided droplets (the disperse, internal or discontinuous phase) and a hydrophobic, immiscible liquid (an 'oil') as the matrix in which these droplets are suspended (the nondisperse, continuous or external phase). Such emulsions are termed 'water-in-oil' (W/O). This has the advantage that the entire aqueous phase containing the biochemical components is compartmentalized in discreet droplets (the internal phase). The external phase, being a hydrophobic oil, generally contains none of the biochemical components and hence is inert.

The emulsion may be stabilized by addition of one or more surface-active agents (surfactants). These surfactants are termed emulsifying agents and act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents. Suitable oils include light white mineral oil and non-ionic surfactants, such as sorbitan monooleate (Span™80; ICI) and polyoxyethylenesorbitan monooleate (Tween™80; ICI).

The use of anionic surfactants may also be beneficial. Suitable surfactants include sodium cholate and sodium taurocholate. Particularly preferred is sodium deoxycholate, preferably at a concentration of 0.5% w/v, or below. Inclusion of such surfactants can in some cases increase the expression of the genetic elements and/or the activity of the gene products. Addition of some anionic surfactants to a non-emulsified reaction mixture completely abolishes translation. During emulsification, however, the surfactant is transferred from the aqueous phase into the interface and activity is restored. Addition of an anionic surfactant to the mixtures to be emulsified ensures that reactions proceed only after compartmentalization.

Creation of an emulsion generally requires the application of mechanical energy to force the phases together. There are a variety of ways of doing this which utilize a variety of mechanical devices, including stirrers (such as magnetic stir-bars, propeller and turbine stirrers, paddle devices and whisks), homogenizers (including rotor-stator homogenizers, high-pressure valve homogenizers and jet homogenizers), colloid mills, ultrasound and 'membrane emulsification' devices.

Aqueous microcapsules formed in water-in-oil emulsions are generally stable with little if any exchange of plasmids or protein products between compartments. The technology exists to create emulsions with volumes all the way up to industrial scales of thousands of liters.

The compartment size will vary depending upon the precise requirements of any individual selection process that is to be performed according to the present invention. In all cases, there will be an optimal balance between plasmid library size, the required enrichment and the required concentration of components in the individual compartments to achieve efficient reactivity of the protein products.

The thermostable emulsions used in DEEPid have a mean diameter of around 10 µm, though other geometries may be suitable for proper activity when compartmentalizing cells. However, the compartment size must be sufficiently large to accommodate all of the required components of the biochemical reactions that are needed to occur within the compartment.

EXAMPLES

Example 1

Scheme of DEEPid Selection to Generate DNA Polymerases with Improved Properties

This example provides a general description of how the DEEPid methodology can be applied to generate novel DNA polymerase variants with improved properties, e.g., enhanced abilities to utilize non-natural nucleotides as substrates for polymerization. In this exemplary method, a library of sequences encoding variants of the DPO4 polymerase is subjected to selection for the ability to extend a free 3' end with XNTP substrates (see, e.g., PCT publication no. WO 2016/081871 to Kokoris et al.) With reference to FIG. 1, the selection scheme includes the following steps:

1) Library expression: Bacterial cells are transformed with a library of convertible parental plasmid constructs (i.e. DEEPid plasmids) encoding DPO4 variants and induced to express the variant polymerase proteins. The inventors have surprisingly found that, contrary to the teachings of the prior art, cells must be induced to express polymerase protein prior to compartmentalization in emulsion.

2) Compartmentalization: The induced bacterial cells are compartmentalized with XNTPs, including biotin-XCTP, lysozyme, and a nickase endonculease in water-in-oil emulsion droplets, such that single cells are isolated in individual compartments.

Figure 2:
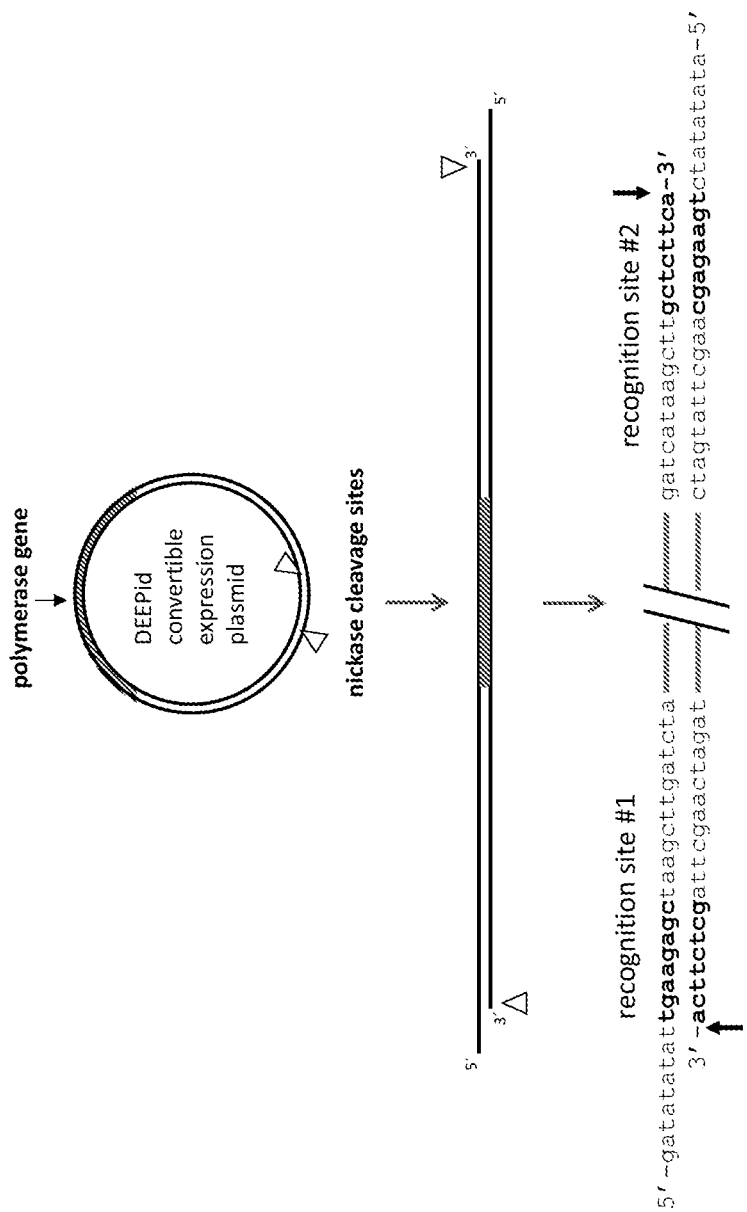
FIG. 2 illustrates one embodiment of a DEEPid convertible parental plasmid (SEQ ID NOS: 1-2).

3) Cell lysis and plasmid digest to produce free 3' ends: Conditions are provided to induce lysozyme-mediated disruption of the bacterial cells, releasing the DEEPid parental plasmids, followed by nickase-mediated digestion at specific recognition sites within the convertible parental plasmids. In this example, the DEEPid plasmid has been engineered to contain two closely-spaced nickase sites positioned on opposite strands of the plasmid. Nickase digestion of the parental plasmid thus linearizes the plasmid, providing two single-stranded 5' overhangs (OHs) and two free 3' ends. The length of the 5'OHs is determined by the spacing between the two nickase sites. One exemplary convertible DEEPid plasmid is illustrated in FIG. 2. Here, two recognition sites for cleavage by the nickase, BstNt.BspQ1, (5' GCTCTTCA 3') have been engineered into opposite strands of the plasmid, separated by 16 base pairs. Nickase-mediated digestion of the plasmid thus produces two 5' overhangs, 16 nucleotides in length, which serve as templates for polymerase-mediated extension of the two 3' ends.

4) Tagging of plasmid: The 5' OHs of the linearized parental plasmids serve as templates for DPO4 polymerases during extension of the two free 3' ends. Polymerase variants capable of utilizing XNTPS as substrates will incorporate biotin-labeled XCTP into the linearized parental plasmid. Conversely, DPO4 variants incapable of utilizing XNTPs as substrates will not modify the linearized parental, which will thus lack an isolation tag.

5) Enrichment: The emulsions are broken and the biotinylated plasmids are recovered via binding to streptavidin-coated beads.

6) Amplification: The DPO4-encoding sequences from the recovered plasmids are PCR amplified and recloned, followed by functional screening of the DPO4 variants or another round of DEEPid selection.

Example 2

DEEPid Plasmid Tagging is Dependent on Active Polymerase

This example demonstrates that a convertible parental plasmid construct can be linearized in emulsion to provide a template for modification (e.g., "tagging") by DNA polymerase. Furthermore, this example demonstrates that tagging of linearized template is dependent upon polymerase activity.

In this experiment, the convertible parental plasmid, "DEEPid48", has been engineered to contain two nickase cleavage sites spaced 16 base pairs apart on opposite strands of the plasmid pET26. Nickase-mediated cleavage of DEEPid48 thus generates a linearized plasmid with two 5' OHs each 16 nucleotides in length, which provide templates for polymerase-mediated extension of the two free 3' ends. T7pLysY cells were transformed with parental plasmids encoding either wild-type DPO4 polymerase ("wt"), a catalytically inactive DPO4 variant ("null") or a DPO4 variant that displays high extension activity with XNTP substrates ("MOTHRA").

Transformed cells were induced to express polymerase protein then compartmentalized in emulsion at an estimated concentration of one cell per 10 μm emulsion droplet. The emulsion reactions were set up such that droplets also contained natural dNTPs, including biotinylated dCTP, lysozyme, and the nickase, Nt.BspQ1. In emulsion, compartmentalized cells are lysed by lysozyme to release both the parental plasmid and the polymerase protein.

Figure 3:
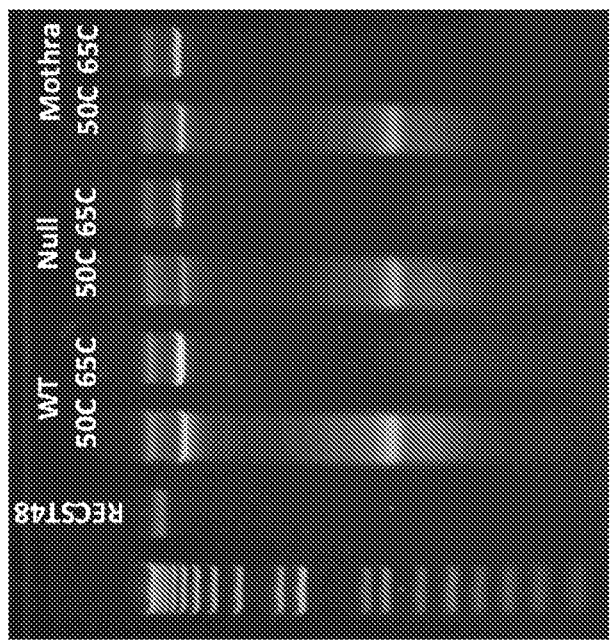
FIG. 3 is a gel showing conversion of a DEEPid expression plasmid into a linearized template.

The parental plasmid is then available for nickase-mediated digestion to convert the plasmid into a linearized template with two free 3' ends that can be extended by the polymerase utilizing the dNTP substrates. Incorporation of biotin-dCTP introduces a tag that enables polymerase-modified plasmids to be selectively isolated. Extension reactions were run for 2 hrs at either 50° C. or 65° C. and digest and extension products were analyzed by gel electrophoresis. As shown in FIG. 3, the parental plasmid, DEEPid48, has indeed been converted into a linearized polynucleotide while compartmentalized with the nickase endonuclease in emulsion droplets.

Next, extension products were enriched by purification of biotinylated plasmid from the reaction mixtures using streptavidin-coated paramagnetic beads. Isolated products were eluted off the beads and quantified by qPCR. To assess polymerase activity, the crossing point ("CP") values of the wild-type or MOTHRA reactions were compared to those of the catalytically inactive "null" polymerase. Results are shown in FIG. 4, where the "background" values represent the ratio of the activity of the null mutant to that of either WT DPO4 or the active MOTHRA variant. These results show that DEEPid plasmid tagging is highly dependent on active polymerase, as very little tagged plasmid is recovered from the null reactions. It was also observed that a higher reaction temperature lowered the background signal, which may reflect greater heat inactivation of endogenous E. coli polymerases. Together, these results demonstrate the successful conversion of parental plasmid into DEEPid template as well as polymerase-dependent extension of the resultant free 3' ends in emulsion droplets to yield a tagged enzyme-encoding polynucleotide product for selective isolation.

Example 3

Polymerase-Dependent Extension with Modified Substrates in a Mock DEEPid Lysate

This example demonstrates that non-natural nucleotide substrates can be incorporated by DPO4 polymerase variants under conditions compatible with the DEEPid methodology.

Bacterial cells expressing the DPO4 variant, PDC42, which has been evolved to incorporate highly substituted XNTP nucleotide analogs, were compartmentalized in emulsion droplets at a concentration of one cell per 10 μm droplet with lysozyme, as described. Emulsion reactions also contained a fluorescent extension oligo hybridized to a short template ("E-oligo"), which enables extension products to be analyzed by gel electrophoresis, and a nucleotide analog substituted with a bulky spermine moiety ("1× spermine dCTP"). Upon lysozyme-mediated cell lysis, the PDC42 enzyme is free to extend the E-oligo with 1× spermine dCTP.

Figure 5:
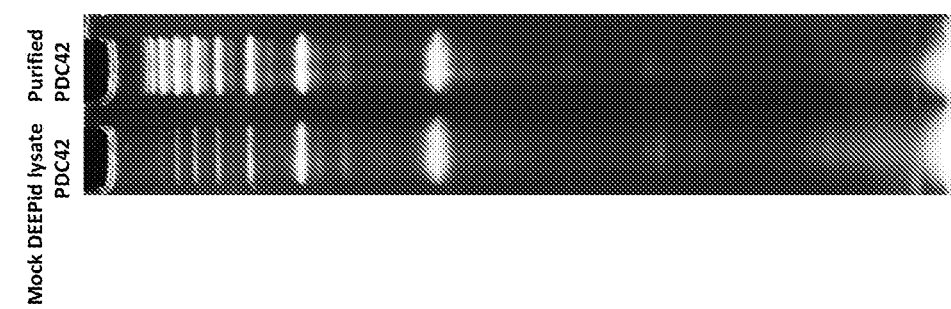
FIG. 5 is a gel showing extension results using a mock DEEPid lysate.
Figure 7A:
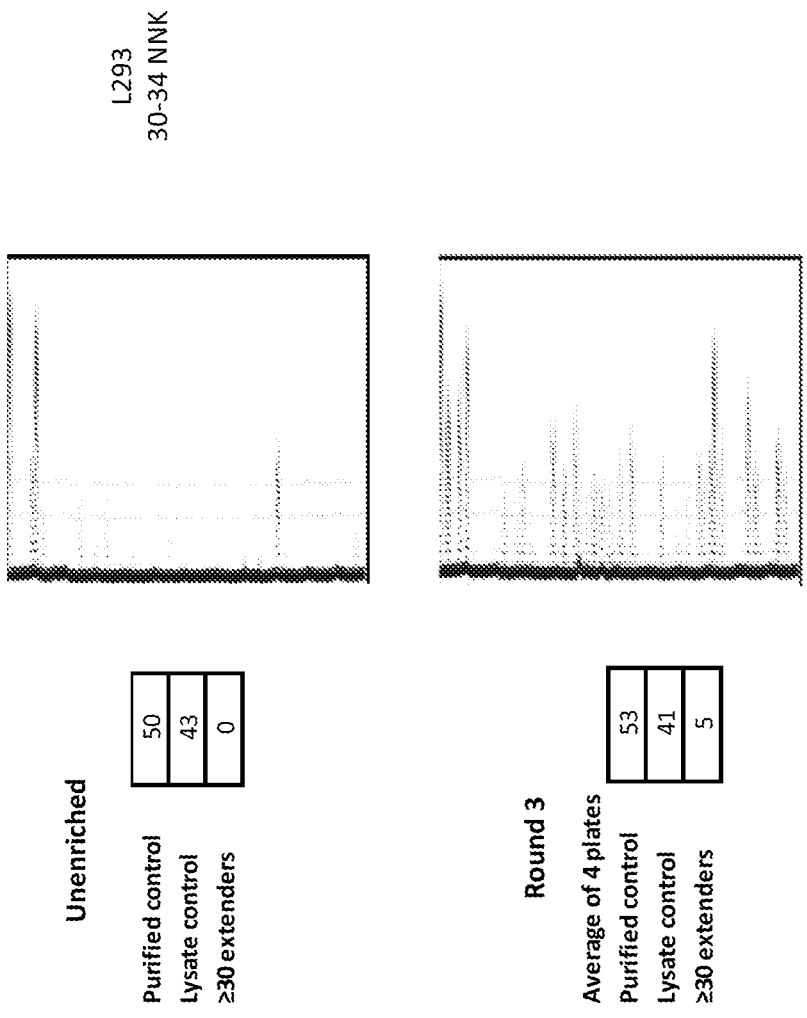
Figure 7B:
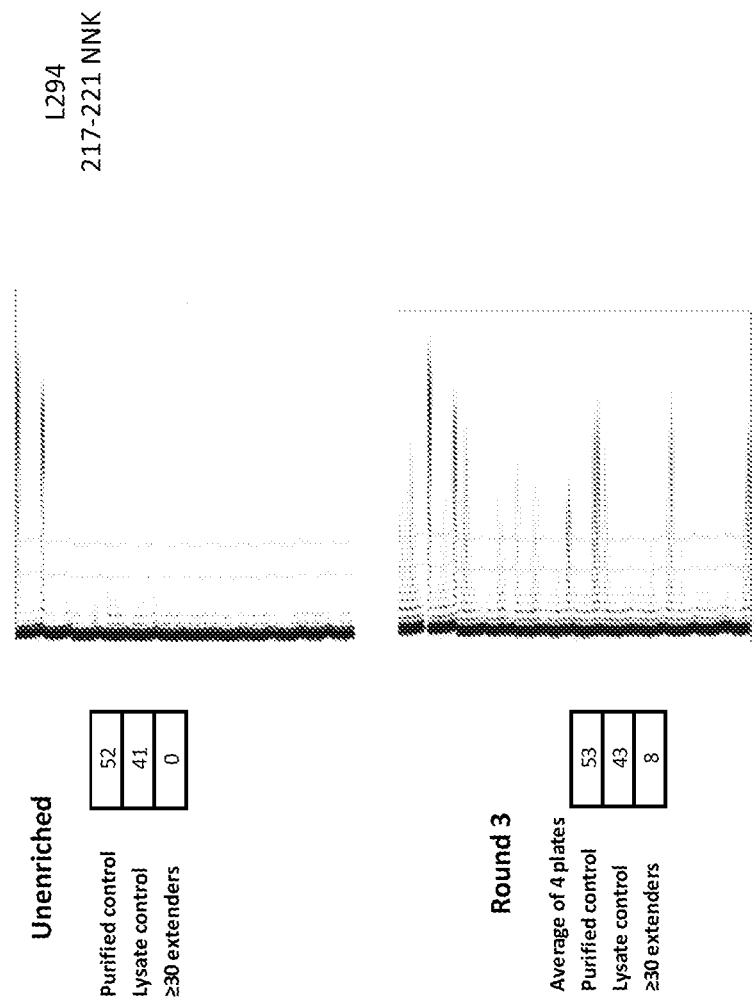
Figure 7D:
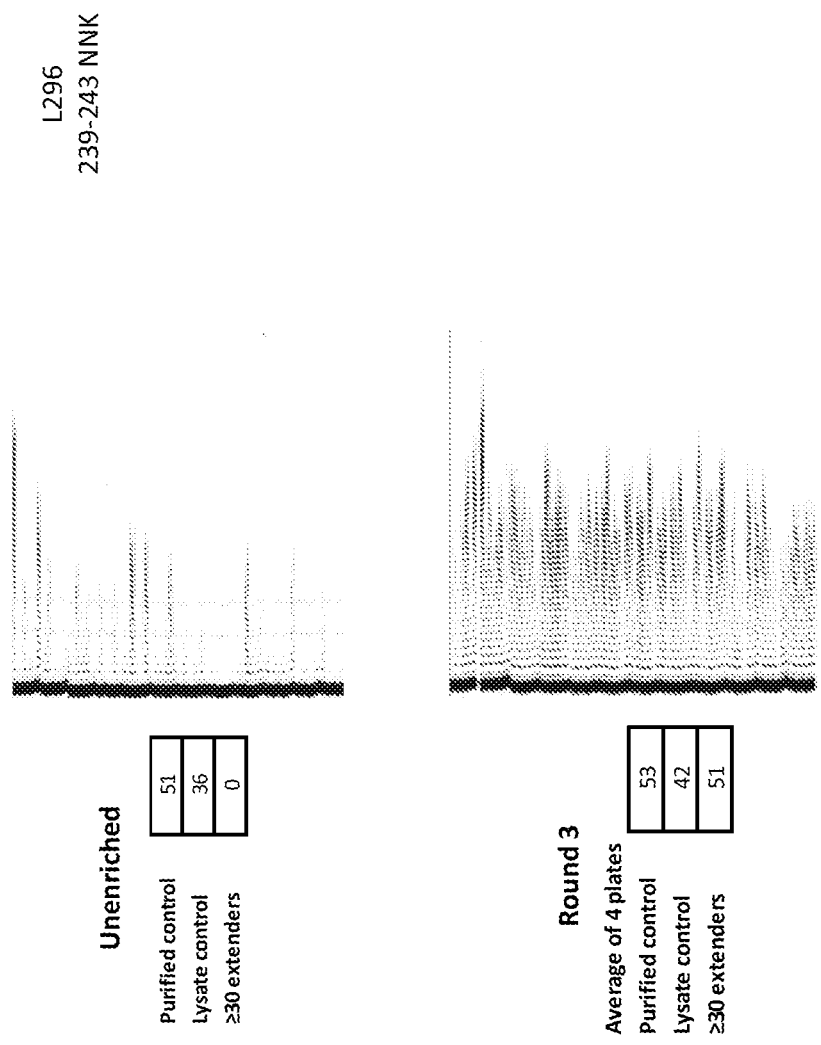

As shown in FIG. 5, when PDC42 polymerase is provided in a mock DEEPid lysate, extension activity is readily detected. These results indicate that the DEEPid reaction conditions are compatible with polymerase activity against challenging substrates, such as highly substituted nucleotide analogs and, therefore, that DEEPid offers a useful means to select for new and useful polymerase variants.

Example 4

Application of the DEEPid Methodology to Libraries of DPO4 Polymerase Variants

To begin selection for DPO4 variants with enhanced abilities to incorporate bulky nucleotide analogs, several libraries of variant polymerases were generated. For site-directed mutagenesis, the PCR-based Q5 mutagenesis kit (NEB) was used in which the either one or both of the primers was represented by a library of variant sequences. The template used for PCR was the DEEPid48 plasmid (see FIG. 2) encoding the backbone polymerase, PDC79, a DPO4 variant that is highly active with XNTP substrates. Primers were designed to generate the following five different libraries: 1) L263 (targeting amino acids 105 and 106); 2) L293 (targeting amino acids 30-34); 3) L294 (targeting amino acids 217-221); 4) L295 (targeting amino acids 232-234 and 236-238); and 5) L296 (targeting amino acids 239-243). Following the Q5 PCR reactions, amplification products were gel purified and circularized in standard KLD reactions. KLD reactions were optimized such that 10-50 ng of DNA would yield on the order of $1-5\times10^6$ transformed colonies following transformation of plasmid products into T7pLys7 bacterial cells to produce plasmid libraries. It was estimated that the L263 library represents ~400 variants, while the L293-L296 libraries represent ~$3.2\times10^6$ variants.

For DEEPid library selection, plasmid libraries were first transformed into T7pLysY cells for protein expression. 1-2 μg plasmid DNA was added to 25 μl cells, which were incubated on ice for 5' then subjected to electroporation. 1 mL of pre-warmed SOC media was then added to the cells and the recovery cultures were incubated for at least an hour at 37° C. Primary cultures were started by inoculating 700 μl recovery culture into 100 mL media and grown to $OD_{600}$ ~0.5. Protein expression was then induced by adding IPTG and incubating the cultures overnight at 25° C. Library expressor cells were harvested from the induction cultures, washed, and resuspended in buffer for immediate use or frozen for storage.

For DEEPid plasmid tagging in bulk emulsion, the following solutions were initially prepared fresh: 1) XNTP mix: 150 pm of XATP (ppo(opoΞ)nAΞ RQLNDDXXXXXXXYCCCTCTXCCCTCTL), XGTP (ppo(opoΞ)nGΞ RQLNDDXXXXXXXYCCCTCTXCCCTCTL), and XTTP (ppo(opoΞ)nTΞ RQLNDDXXXXXXXYCCCTCTXCCCTCTL), and 50 pm of biotin-XCTP (ppo(opoΞ)nCΞ

RQLNDDXXXXXXXYCCCTCTXCCCTCTL(biotin)); 2) 10M urea; 3) 10 mg/mL egg white lysozyme; and 4) 200 mM $MnCl_2$. Next, the following master mix was prepared: 20 mM Tris OAc pH 8.32, 200 mM NH4OAc pH 6.88, 20% PEG 8000, 7.5% DMSO, 3 mM PP-60, 4 mM $MnCl_2$, 1 M urea, and 0.5 mM PMSF. Then, emulsifications were initiated by adding 10 reaction volumes of oil/surfactant to a 2 mL cryovial with a stir bar, and cooling on ice. A "master mix A" was then prepared with 3.19 μL of master mix and 1 μL expresser cells added just prior to emulsification and a "master mix B" was prepared with 3.19 μL of master mix, 1 μL Nt.BspQI (10 U/μL), 1 μL lysozyme solution, and 0.96 μL of the XNTP mix. The bulk hydrocarbon emulsion reactions were intended to produce droplets with an average diameter of 10 μM and volume of 0.523 pL with a target cell concentration of 0.1 cell/droplet. To compartmentalize expressor cells, mixes A and B were mixed and then immediately added to the oil/surfactant and stirred at 700 RPM for 5 min on ice to create an emulsion. The emulsion was transferred to a 1.5 mL screwcap tube, sealed with parafilm, and incubated at 50° C. for 15 min, followed by 42° C. for 20 min.

To break the emulsion and purify plasmid, 5 volumes of QIAquick PCR purification kit buffer B was added and the mixture was vortexed for 15 seconds and centrifuged at 3000×g for 1 minute to remove excess oil. Samples were loaded into a QIAquick column, spun for 1 min at 17,900×g, washed twice with 300 μL 2 M GuCl, spun 1 min at 1,500×g, washed with 740 μL Buffer PE, spun twice for 1 min at 17,900×g to remove residual wash buffer, and eluted with 100 ul Buffer EB. 2 μL of the eluted sample was added to 18 μL PCR-grade water for qPCR analysis. Next, the sample was subjected to a succinylation reaction to reverse the positive charges on the cationic regions of the XNTP tethers. Without being bound by theory, the inventors speculate that reversing the positive charges on the XNTP substrates weakens the interaction between DNA and unincorporated, free biotin-XNTP, thereby reducing background. For succinylation, $NaHCO_3$, pH 9 was added to samples at a final concentration of 100 mM followed by succinic anhydride at a final concentration of 333.33 mM. Reactions were incubated at 55° C. for 20 minutes and samples were washed using the QIAquick purification protocol described above.

To isolate biotinylated plasmids, the kilobaseBINDER kit (Thermo Fisher Scientific) was used. Dynabeads were resuspended by vortexing the bottle for 30 seconds and 5 μL (50 μg) of resuspended beads were transferred to a PCR tube and placed on a magnet for 2 minutes. The supernatant was removed while the tube remained on the magnet. The tube was removed from the magnet and 20 μL Binding Solution was added along the inside wall of the tube where the beads collected, which were resuspend by pipetting. The sample was placed on the magnet for 2 minutes and the supernatant was again removed. Beads were resuspended in 98 μL Binding Solution. 98 μL of a solution containing the biotinylated DNA was added to the resuspended beads, mixed, and incubated at room temperature for 3 hours on a roller to keep the beads in suspension. The tube was placed on the magnet to remove supernatant, which was retained. The Dynabeads/DNA-complex was washed twice in 40 μL Washing Solution and placed on the magnet for 2 minutes to discard supernatant each time. Samples were resuspended in 40 μL 10 mM Tris/0.1% Tween-20, transferred to fresh tubes, and placed on the magnet for 2 minutes to discard supernatant. Beads were resuspended in 166.67 μL 10 mM Tris/0.1% Tween-20 to a final bead concentration of 0.3 μg/μL To quantify plasmid concentration in pre-enrichment samples, post-succinylation samples, and post-enrichment samples, a qPCR protocol was used. A standard curve was generated with serial dilutions of the 6388 bp DEEPid48 plasmid, from 0 to 200,000 copies per reaction. Each test sample was diluted 1:10 and 1:1000 for qPCR reactions. Reactions were run with the LightCycler FastStart Enzyme and FastStart rxn mix, SYBR Green I, and 5 μM forward and reverse DEEPid48 primers for 40 cycles of 95° C. for 10 seconds, 55° C. for 5 seconds, and 72° C. for 10 seconds.

The enriched population of post-selection clones was then PCR amplified from bead eluates for re-cloning into the DEEPid48 expression vector. In order to preserve the diversity of the library, the qPCR data was used to determine the volume of beads to be used in the PCR amplification. The Q5 Hot Start PCR kit and 0.5 μM of forward and reverse primer specific for the DEEPid48 vector were used to amplify the variant library sequences from 25 μg bead-bound DEEPid48 plasmid. 30 PCR cycles were run at 98° C. for 10 seconds, 66° C. for 30 seconds, and 72° C. for 45 seconds. PCR products were cleaned-up with QIAquick kits before gel purification. Purified PCR products were then re-cloned into the DEEPid48 vector by restriction digest with XhoI and followed by ligation with the linearized vector cut with the same enzymes. At this point, the ligated DNA was used either to transform cells for post-enrichment functional analysis or for cycling back into DEEPid for another round of selection/enrichment. FIG. 6 shows a representative example of the results from three rounds of DEEPid applied to the 105/106 library. Controls include the DPO4 polymerase variants, C342R1 (a full length, catalytically inactive, negative control DPO4 variant) C417R1 (positive control), and C422R1 (an inactive truncated variant, serving as a second negative control). A consistent trend towards lower crossing points with each round of DEEPid was observed with two independent selections of the 105/106 library, indicating progressive enrichment of active polymerases. As expected, no similar enrichment was observed in the negative control selection.

Example 5

Sequences of Novel DPO4 Polymerase Variants Selected Via DEEPid Methodology

After three rounds of DEEPid, functional extension assays were performed in a 96-well plate format to identify the most active DPO4 variant polymerases. For functional screening, primary cultures were started for 94 independent clones and grown overnight. The following day, induction cultures were started in the wells of 96-well plates. Three hours following inoculation, cells were induced to express protein for 4 hours, followed by spinning and washing at 4° C. Cells were lysed with lysozyme in the presence of PMSF and kept on ice prior to functional analysis. 96-well plate polymerase screening extension assays were performed by assessing the ability of the variants to extend a template-bound primer with dNTP-OAc (deoxynucleotides modified with an acetate moiety) substrates. The template used was a mixed-base oligomer that provides for extension products of up to 60 nucleotides. Extension products were analyzed by gel electrophoresis to detect the labeled primer. FIGS. 7A-7D show representative gels with extension products synthesized by variants selected after three rounds of DEEPid from four different libraries. The numbers next to the gels indicate the number of variants from a single 96-well plate capable of synthesizing extension products greater than 30 nucleotides in length. It was consistently observed that unenriched populations yield no active variants, while just three rounds of DEEPid produces a significant enrichment of active variants. Several of the most active variants from each library were sequenced. The sequences of these variants are set forth in Tables 1-4 below with the CO418 parental sequence at the top for reference.

TABLE 1

(L293: mutagenesis of amino acids 30-34)

| | ID | | | | | |
|---|---|---|---|---|---|---|
| 30 | 31 | 32 | 33 | 34 | | |
| | | CO418 | | | | |
| V | C | V | F | S | extensions | control |
| SGM-491_83 V | C | V | deletion | G | 30 | 39 |
| SGM-492_11 V | L | V | S | T | <30 | 41 |
| SGM-492_64 V | C | G | P | D | <30 | 41 |

TABLE 2

(L294: mutagenesis of amino acids 217-221)

| | ID | | | | | |
|---|---|---|---|---|---|---|
| 217 | 218 | 219 | 220 | 221 | | |
| | | CO418 | | | | |
| I | G | E | A | K | extensions | control |
| SGM_494_34 V | G | A | P | L | 45 | 45 |
| SGM_494_54 V | G | S | T | E | 40 | 45 |
| SGM_495_19 I | G | P | H | L | 46 | 44 |
| SGM_495_46 I | G | E | A | K | 45 | 44 |

TABLE 3

(L295: mutagenesis of amino acids 233-234 and 236-238)

| | ID | | | | | |
|---|---|---|---|---|---|---|
| 233 | 234 | 236 | 237 | 238 | | |
| | | CO418 | | | | |
| Y | N | P | I | R | extensions | control |
| SGM_498_83 L | C | P | L | R | 36 | 40 |

TABLE 4

(L296: mutagenesis of amino acids 239-243)

| | ID | | | | | |
|---|---|---|---|---|---|---|
| 239 | 240 | 241 | 242 | 243 | | |
| | | CO418 | | | | |
| T | R | V | R | K | extensions | control |
| SGM_500_02 P | T | R | V | G | 41 | 46 |
| SGM_500_62 A | S | V | R | R | 46 | 46 |
| SGM_500_74 E | K | R | R | R | 44 | 46 |

Example 6

Application of DEEPid to Enrich for Specificity

This Example demonstrates how DEEPid may be adapted to enrich for a specific enzymatic activity by engineering molecular stresses, or 'challenges', into a DEEPid parental plasmid. In this exemplary method, DPO4 polymerase variants are selected for the ability to extend a growing strand over ten nucleotides in length. A DEEPid parental "challenger" plasmid is first designed with the following features: 1) two nickase recognition sites located on opposite strands of the circular plasmid; 2) a molecular "challenge" sequence located on the 3' side of each nickase site; in this example, the challenge is a sequence of at least ten base pairs that lacks a G/C base pair; and 3) at least one G/C base pair located at the 3' end of each challenge sequence. A library of DPO4 variants is expressed by transforming bacterial cells with the library of DEEPid challenger plasmids and inducing expression of the encoded variant polymerase proteins. The induced bacterial cells are compartmentalized with XNTPs, including biotin-labeled XGTP, lysozyme, and a nickase endonculease in water-in-oil emulsion droplets, such that single cells are isolated in individual compartments. Conditions are then provided to induce lysozyme-mediated disruption of the bacterial cells, releasing the DEEPid challenger plasmids, followed by nickase-mediated digestion at the two specific recognition sites within the convertible plasmids. Nickase digestion of the parental plasmid linearizes the plasmid, providing two single-stranded 5' overhangs (OHs) over ten nucleotides in length, in which the first C in the sequence follows the ten base challenge sequence. These 5' OHs of the linearized parental plasmids serve as templates for DPO4 polymerases during extension of the two free 3' ends. Polymerase variants capable of processive polymerization of a product over ten nucleotides in length will extend across the ten base "challenge" template sequence and incorporate biotin-labeled XGTP into the nascent strand upon reaching the first C in the template. Conversely, DPO4 variants incapable of processive polymerization under these conditions will not incorporate biotin-XGTP into the challenger plasmid, which will thus lack an isolation tag. The emulsions are then broken and the biotinylated plasmids are recovered via binding to streptavidin-coated beads. The DPO4-encoding sequences from the recovered plasmids are PCR amplified and recloned, and may be followed by another round of DEEPid challenge selection.

While this Example describes DEEPid challenge selection with a particular template, other embodiments of the present invention contemplate serial DEEPid challenge selection under other stressor conditions. For example, serial DEEPid challenge selection may be used to select for specific activities in the presence of particular co-factors, temperatures, additives, and the like.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet including U.S. Patent Application No. 62/401,780 filed on Sep. 29, 2016, and U.S. Patent Application No. 62/412,693, filed on Oct. 25, 2016, are incorporated herein by reference, in their entireties. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for the selection of an enzyme capable of modifying a nucleic acid, wherein the method is not dependent on the complete replication of the enzyme-encoding gene, the method comprising the steps of:
   (a) providing a parent nucleic acid encoding an enzyme of interest, wherein the parent nucleic acid provides the gene sequence of the enzyme of interest, wherein the enzyme of interest is a DPO4 DNA polymerase, and wherein the parent nucleic acid is provided in a host cell;
   (b) providing conditions to induce the host cell to produce the enzyme of interest such that the host cell comprises the parent nucleic acid together with the enzyme of interest;
   (c) following production of the enzyme of interest by the host cell, compartmentalizing the host cell, wherein the step of compartmentalizing the host cell comprises forming a water in oil emulsion droplet, wherein the water in oil emulsion droplet comprises the host cell together with a lysozyme, a nickase endonuclease, and XNTPs, wherein the XNTPs each comprise a selectively cleavable bond and a tether that is attached at positions that allow for controlled expansion of the XNTP by intra-XNTP cleavage of the selectively cleavable bond; and wherein the lysozyme is capable of lysing the host cell to release the parent nucleic acid and the enzyme of interest;
   (d) providing conditions to cleave at least one strand of the parent nucleic acid to provide at least one free 3' end and at least one free 5' end;
   (e) providing conditions such that the at least one free 3' end or the at least one free 5' end of the parent nucleic acid is modified by the enzyme of interest to yield a modified parent nucleic acid, wherein the modified parent nucleic acid comprises XNTPs and a molecular tag; and
   (f) isolating the modified parent nucleic acid.

2. The method of claim 1, wherein the conditions to cleave the at least one strand of the parent nucleic acid to provide the at least one free 3' end or the at least one free 5' end of the parent nucleic acid further comprise exposing the parent nucleic acid to the nickase endonuclease.

3. The method of claim 1, wherein the nickase endonuclease is Nt.BspQ1.

4. The method of claim 1, wherein the conditions to cleave the at least one free 3' end or the at least one free 5' end of the parent nucleic acid linearizes the parent nucleic acid.

5. The method of claim 1, wherein the host cell is a bacterial cell.

* * * * *

SEQUENCE LISTING

```
<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: Synthetic sequence

<400> SEQUENCE: 1
gatatatatt gaagagctaa gcttgatcta gatcataagc ttgctcttca            50

<210> SEQ ID NO 2
<211> LENGTH: 50
<212> TYPE: DNA
<213> ORGANISM: Artificial Sequence
<220> FEATURE:
<223> OTHER INFORMATION: Synthetic sequence

<400> SEQUENCE: 2
atatatatct gaagagcaag cttatgatct agatcaagct tagctcttca            50
```